United States Patent
Gregory

(10) Patent No.: US 8,858,520 B2
(45) Date of Patent: Oct. 14, 2014

(54) TEMPORARY OSTOMY APPLIANCE

(75) Inventor: Christopher Gregory, Wrightstown, PA (US)

(73) Assignee: Convatec Technologies Inc., Las Vegas, NV (US)

(*) Notice: Subject to any disclaimer, the term of this patent is extended or adjusted under 35 U.S.C. 154(b) by 282 days.

(21) Appl. No.: 12/988,826

(22) PCT Filed: Apr. 21, 2009

(86) PCT No.: PCT/US2009/041237
§ 371 (c)(1),
(2), (4) Date: Oct. 21, 2010

(87) PCT Pub. No.: WO2009/131992
PCT Pub. Date: Oct. 29, 2009

(65) Prior Publication Data
US 2011/0040231 A1    Feb. 17, 2011

Related U.S. Application Data

(60) Provisional application No. 61/046,999, filed on Apr. 22, 2008.

(51) Int. Cl.
*A61F 5/44*     (2006.01)
*A61F 5/445*    (2006.01)

(52) U.S. Cl.
CPC ...................................... *A61F 5/445* (2013.01)
USPC .......................................................... 604/346

(58) Field of Classification Search
USPC .......................................................... 604/346
See application file for complete search history.

(56) References Cited

U.S. PATENT DOCUMENTS

| | | | |
|---|---|---|---|
| 3,581,732 A * | 6/1971 | Ruiz | 600/435 |
| 4,346,712 A | 8/1982 | Handa | |
| 5,273,529 A * | 12/1993 | Idowu | 604/500 |
| 5,312,343 A | 5/1994 | Krog | |
| 5,417,657 A * | 5/1995 | Hauer | 604/103.02 |
| 5,813,976 A | 9/1998 | Filipi | |
| 6,461,327 B1 * | 10/2002 | Addis et al. | 604/101.04 |
| RE38,711 E * | 3/2005 | Igaki et al. | 606/198 |
| 7,037,344 B2 * | 5/2006 | Kagan et al. | 623/23.65 |
| 7,048,906 B2 * | 5/2006 | Lin et al. | 424/9.2 |
| 7,220,284 B2 * | 5/2007 | Kagan et al. | 623/23.65 |
| 7,722,583 B2 * | 5/2010 | Kim et al. | 604/317 |
| 7,780,641 B2 * | 8/2010 | Ferko | 604/332 |
| 2001/0001114 A1 | 5/2001 | Tsugita | |

(Continued)

FOREIGN PATENT DOCUMENTS

| EP | 0 168 967 A1 | 1/1986 |
|---|---|---|
| EP | 1779823 | 5/2007 |

*Primary Examiner* — Susan Su
*Assistant Examiner* — Guy K Townsend

(57) ABSTRACT

A temporary ostomy appliance is disclosed, including a catheter for extending through the abdominal wall into the intestine. The catheter may be a transcecal catheter for extending through the cecal valve into the ileum. A portion of a catheter that extends through the cecal valve is made collapsible when the catheter is empty. The collapsed portion expands to permit passage of effluent. A balloon carried on the catheter is preformed with a shape and size in order to permit inflation without elastic stretching of the balloon wall material. A filament is provided for permitting a portion of the catheter to be fastened to internal body tissue by surgical sutures or staples. In order to release the fastening without further surgery, the filament is withdrawn by pulling on a proximal portion outside the body.

29 Claims, 6 Drawing Sheets

(56) References Cited

U.S. PATENT DOCUMENTS

| | | |
|---|---|---|
| 2001/0037085 A1 | 11/2001 | Keith |
| 2002/0082610 A1 | 6/2002 | Cioanta |
| 2002/0193806 A1* | 12/2002 | Moenning et al. ............ 606/108 |
| 2004/0111061 A1* | 6/2004 | Curran ........................ 604/174 |
| 2004/0148034 A1* | 7/2004 | Kagan et al. ............... 623/23.65 |
| 2005/0038415 A1 | 2/2005 | Rohr |
| 2005/0054996 A1 | 3/2005 | Gregory |
| 2005/0240279 A1* | 10/2005 | Kagan et al. ............... 623/23.65 |
| 2006/0189951 A1* | 8/2006 | Kim et al. ..................... 604/327 |
| 2008/0312614 A1* | 12/2008 | Ferko ........................... 604/332 |

* cited by examiner

TEMPORARY OSTOMY APPLIANCE

FIELD OF THE INVENTION

The present invention relates to a temporary ostomy appliance including a catheter for extending through the abdominal wall into the intestine. The invention is especially, although not exclusively, directed to a transcecal appliance that extends through the abdominal wall into the large intestine, and through the cecal valve into the ileum.

BACKGROUND TO THE INVENTION

There are many occasions where a temporary ileostomy would be desirable to drain effluent from the small intestine for a temporary period of time, to enable analysis, repair and/or healing at a downstream site in the large intestine. Typically, a temporary ileostomy involves two surgical operations, namely (i) a colon resection during which the abdominal wall and intestinal wall are opened to create the temporary ileostomy diversion, and (ii) a later closure operation (laparotomy) which closes the openings in the intestinal wall and the abdominal wall to restore the normal intestinal route for effluent. The second operation normally occurs around 4 to 6 months after the first. However, the combination of two serious surgeries has a high morbidity and mortality problem, and the costs of two such serious operations are very high. The risks and costs mean that a temporary ileostomy is not used as extensively as it might be in all cases. Also, the risks of the second serious operation may be too high for many patients resulting in the temporary becoming a permanent ostomy.

EP-A-1779823 describes a transcecal ileostomy set intended to addresses these problems. Only the single initial surgical operation is needed. The catheter is inserted during the surgery to treat the large intestine. The catheter enters the body through an incision through the abdominal wall and then the intestine via an incision made in the large intestine wall, and extends through the cecal valve into the small intestine. A feature of EP-A-1779823 is that catheter is not directly fastened or sealed to the intestine, e.g., by sutures or surgical staples that would require a second surgical operation to remove. Instead, the catheter has two inflatable balloons, one of either side of the cecal valve. A blocking balloon on the small intestine side obstructs the small intestine, and causes effluent to be diverted into the catheter. A fixation balloon on the large intestine side fixes the catheter with respect to the large intestine. There is no disclosure of the balloon construction, which presumably is conventional using thin elastic material that stretches as the balloon expands. A bioresorbable loop passes around the opening in the large intestine wall, and is fastened to a plastic holder outside the patient's abdominal wall. The holder includes a rotary part for tightening the loop, in order to purse the opening in the large intestine wall around the catheter, and to draw the large intestine wall against the abdominal wall. To remove the catheter, the balloons are deflated, allowing the catheter to be withdrawn without surgery. The bioresorbable loop is then further tightened to purse the incision in the large intestine wall closed.

It would be desirable to further refine a temporary ostomy appliance to improve its characteristics.

SUMMARY OF THE INVENTION

One aspect of the present application provides a transcecal catheter with a collapsible catheter portion intended to sit at the cecal valve. Preferably, the catheter includes non-collapsing catheter portions on either side of the collapsible catheter portion. The collapsible portion may be made of thinner wall material than the non-collapsing portions.

An advantage is that such a catheter can reduce the potential risk of damage to the cecal valve compared to an entirely non-collapsing catheter passing through and sitting at the cecal valve.

Another aspect of the present invention provides a catheter of a temporary ostomy appliance with an inflatable balloon. The catheter may optionally be a transcecal catheter. The inflatable balloon is made of flexible material formed (e.g., molded) in a pre-inflated shape such that, in that shape, the wall material of the balloon does not stretch elastically. In use, the balloon is intended to be inflated to size up to (or smaller than) the pre-inflated shape. The balloon may be a blocking balloon and/or a fixation balloon as used in EP-A-1779823, or it may some other balloon of a catheter.

An advantage of such balloon construction is that it generally enables lower inflation pressures to be used inside the balloon, because it is not necessary to overcome the elastic return forces in elastic material that would generally act against inflation. Also, the forces applied to the surrounding body tissue are generally more predictable and controllable, as this is equal to the inflation pressure. Minimizing the pressure on the inside of the balloon minimizes potential harmful pressure on mucosal tissue.

Another aspect of the present invention relates to facilitating a suture and or staple connection between internal body tissue and a catheter of a temporary ostomy appliance, which connection is releasable selectively without additional surgery. The catheter may be a transcecal catheter. This aspect of the invention provides a filament that extends from a proximal portion of the catheter, and is exposed to extend as at least one bridge feature between respective eyes. The suture/staple may be fastened to this bridge feature of the filament. At a subsequent time, when it is desired to unfasten the connection, the filament is withdrawn from the eyes by pulling from the proximal portion of the catheter. This aspect may be used independently, or in combination with an inflatable balloon, for forming a seal or fastening between a portion of the catheter, and internal body tissue.

In any aspect of the invention, the catheter may include a proximal portion that passes through the abdominal wall, to outside the body.

Additional objects, features and advantages of the invention will be apparent from the following description of preferred embodiments. Any of the following features may be omitted, mixed and combined in any permutation. Protection is claimed for any novel feature or idea described herein and/or illustrated in the drawings, whether or not emphasis has been placed thereon.

DETAILED DESCRIPTION OF PREFERRED EMBODIMENTS

Figure 1:
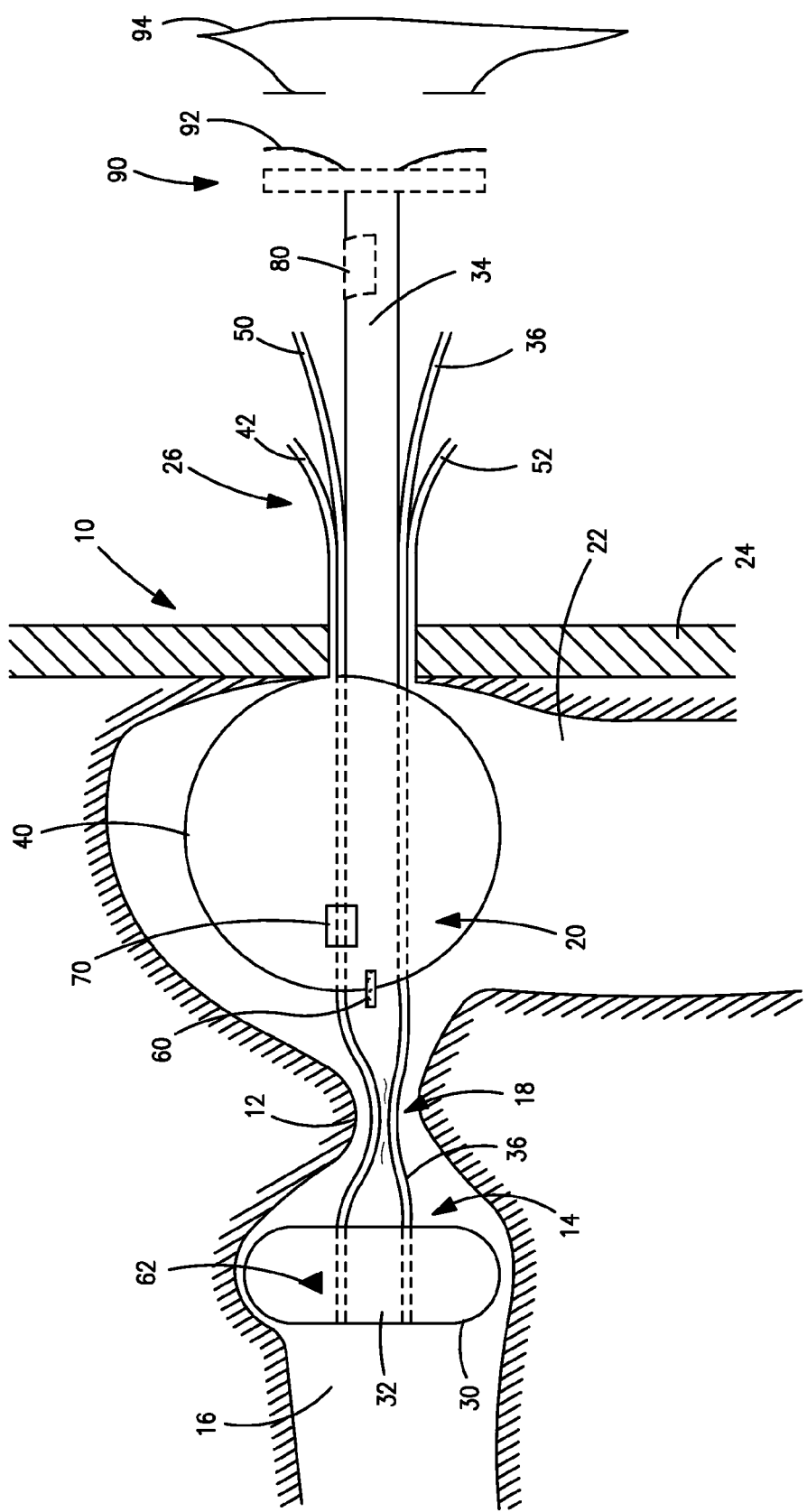
FIG. 1 is a schematic sectional view showing a first embodiment of a temporary ostomy appliance in the form of a transcecal ileostomy appliance, in situ.

The same reference numerals denote similar or equivalent features in each embodiment. Reference is made to basic details of a transcecal ileostomy set described in EP-A-1779828, the contents of which are incorporated herein by reference.

Referring to FIG. 1, a first embodiment of temporary ostomy appliance is a transcecal ileostomy appliance comprising a catheter 10 intended for insertion through the cecal valve 12 of the intestine. The catheter 10 includes a first distal portion 14 intended to be received in the ileum 16, a second portion 18 intended to sit at the cecal valve 12, a third portion 20 intended to be received in the large intestine 22, a fourth portion 25 intended to pass through the abdominal wall 24, and a fifth proximal portion 26 intended to extend outside the body. The catheter 10 is made of any suitable material including, for example, silicone and/or polyurethane.

An inflatable blocking balloon or cuff 30 is optionally provided at the first distal portion 14 for obstructing the ileum 16, and causing effluent to be diverted through an aperture 32 into a drainage lumen 34 of the catheter 10. A blocking balloon inflation lumen 36 communicates with the blocking balloon 30 for inflation and deflation of the blocking balloon 30. Additionally or alternatively, a fixation balloon 40 is optionally provided at the third portion 20 for positively locating the catheter 10 with respect to the large intestine 22. A fixation balloon inflation lumen 42 communicates with the fixation balloon 40 for inflation and deflation of the fixation balloon 40.

Figure 4:
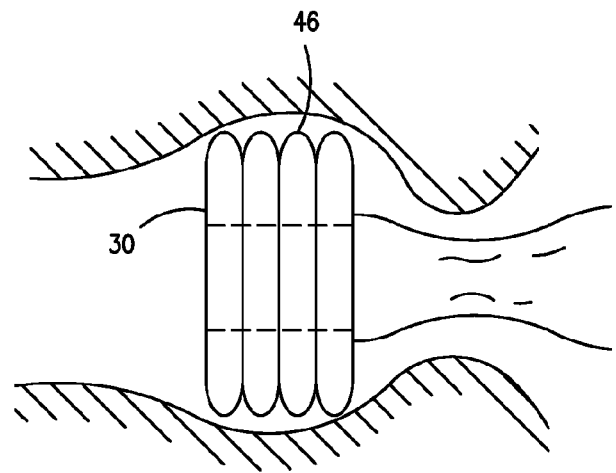
FIG. 4 is a schematic sectional view showing an oversized balloon on the catheter.

Although the balloons 30, 40 may be elastically expandable, at least one of the balloons 30, 40 is preferably made to be substantially non-stretching in use. Referring to FIG. 4, the respective balloon 30, 40 is pre-formed (e.g., pre-molded) of flexible material, into a shape and size that is at least as big as the volume desired to be filled by the balloon 30, 40. Prior to insertion of the catheter 10, the material of the balloon 30, 40 is folded down to a collapsed form. When the catheter 10 is inserted in situ, and the balloon 30, 40 inflated, the balloon 30, 40 expands without elastic stretching of the material. The balloon 30, 40 may be made of substantially non-elastic material, or the balloon 30, 40 may be made of elastic material that is pre-shaped into a sufficiently large shape that the material will not stretch in use. In one form, the balloon 30, 40 is shaped to be larger than the size and shape of volume to be filled by the balloon 30, 40.

An advantage of such a configuration of balloon is that the inflation pressure required to inflate the balloon is generally less than if the balloon expands elastically. A smaller inflation pressure is extremely advantageous, as it reduces the risk of excessive pressure applied to the surrounding body tissue. This contrasts with, for example, a conventional elastically expanding balloon assumed in EP-A-1779823, in which additional inflation pressure is required to overcome the elastic return force as the balloon material stretches. However, as the inflation pressure increases, so does the risk of excessive pressure applied to surrounding mucosal tissue. The configuration used in the present invention is beneficial for either the blocking balloon 30 or the fixation balloon 40, but is believed to be especially advantageous for the blocking balloon 30 that is desired to fill and seal the ileum 16 in order to block passage of effluent.

In one particular form, the balloon 30 is made to be significantly larger than the ileum 16, such as at least 120% of the size of the ileum 16, or at least 150% of the size of the ileum 16. In one form, the balloon 30 may have a minimum inflated diameter of 20 mm. In use, the balloon 30 is inflated in the ileum 16 to a specific pressure that is determined as safe to tissue, but not to the size that the balloon 30 would be in free space without stretching the balloon material. The balloon wall is sufficiently thin (for example, about 100 microns or less) to enable the balloon 30 to have folds and still effect a good seal against the wall of the ileum 16, without being fully inflated in size, and without elastic or plastic deformation of the balloon wall. As shown in FIG. 4, the oversized balloon 30 may have a wrinkled surface 46 as a result of being molded oversize, but the thinness of the material ensures good sealing contact with the intestinal wall.

Figure 2:
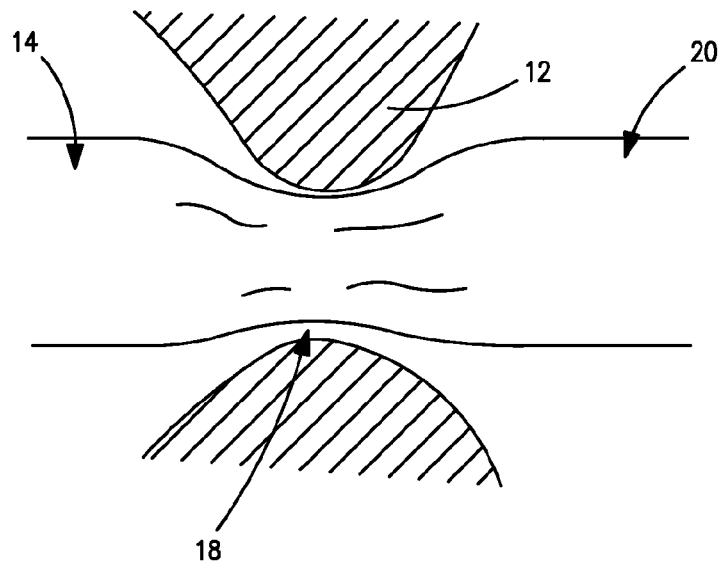
FIG. 2 is a schematic sectional view showing the second portion of the catheter in a collapsed condition.
Figure 3:
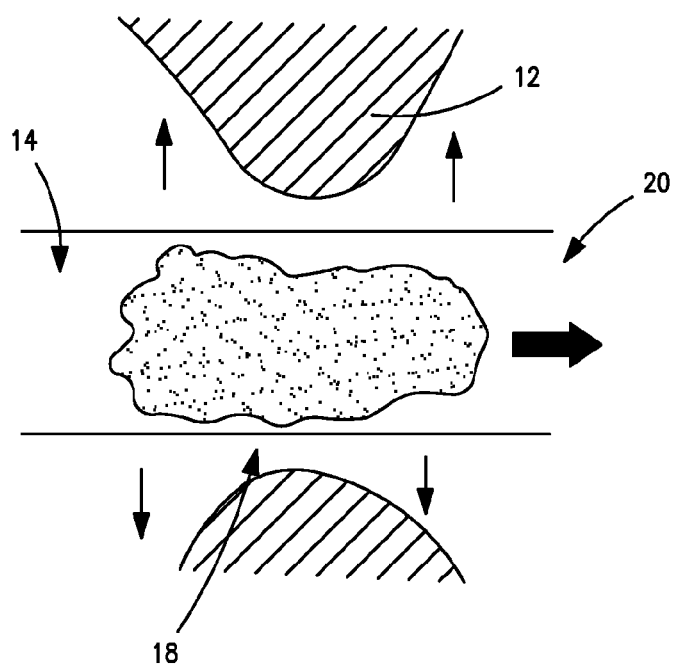
FIG. 3 is a schematic sectional view showing the second portion of the catheter expanding to pass effluent.

Referring to FIGS. 1-3 and 5, another feature of this embodiment is that the second portion 18 of the catheter 10 that sits at the cecal valve 12 is made to be at least partly collapsing. This contrasts to the adjacent first portion 14 and third portions 20 that have a generally self-supporting hollow, tubular shape. The collapsing nature of the second portion 18 allows the cecal valve 12 to adopt a more constricted shape when no effluent is passing (FIG. 2). Upon passage of effluent, the second portion 18 is forced to expand by the effluent (FIG. 3), allowing the effluent to pass from the first portion 14 to the third portion 20, and opening the cecal valve 12. This configuration therefore provides (i) the ability to use a relatively large size catheter 10 for good drainage of effluent without risk of blockage, (ii) avoiding the cecal valve 12 being continuously fully or substantially distended by the presence of the catheter 10, and (iii) maintaining near normal constriction and expansion cycles of the cecal valve 12 responsive to passage of effluent. It is believed that such a configuration can reduce the potential risk of damage to the cecal valve 12. Such a configuration contrasts to the design in EP-A-1779823 in which there is an inherent design limitation in terms of the catheter size versus the potential risk of damage to the cecal valve by the catheter continuously distending the cecal valve to the catheter size.

The second portion 18 may be made at least partly collapsing by having a reduced wall thickness (FIG. 5) compared to the adjacent first portion 14 and/or third portion 20. For example, the second portion 18 may be dimensioned with the same outer diameter as an adjacent portion 14, 20, but with a significantly reduced wall thickness such that the second portion 18 is less self-supporting in shape. This permits the second portion 18 to at least partly collapse when the catheter 10 is empty, and thereby relieve pressure applied to the cecal valve 12.

In one form, the second portion 18 can expand upon passage of effluent to an outer diameter of at least about 1 cm, preferably at least about 1.2 cm. Preferably, such expansion is without extension or stretching of the catheter wall material. The second portion 18 can collapse to a diameter of less than 1 cm when empty. Preferably, such collapsing is without compression of the catheter wall material.

Figure 5:
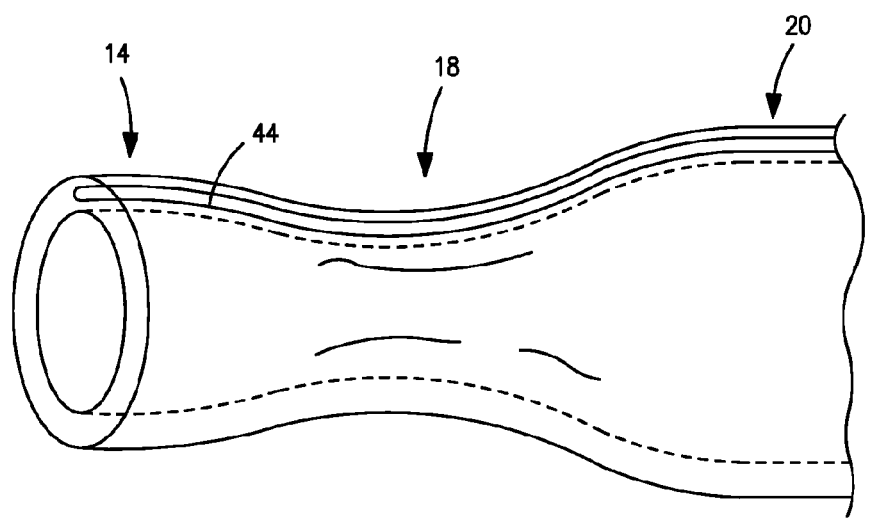
FIG. 5 is a schematic sectional view showing stiffening elements in the catheter wall.

Referring to FIG. 5, another preferred feature of this embodiment is the provision (optionally) of one or more anti-kink elements 44, especially at the collapsing second portion 18 if implemented. While it is desirable for the catheter 10 to be able to collapse where it passes through the cecal valve 12, it is preferable that at least the collapsing second portion 18 (and optionally one, more, or all of the other catheter portions) resist significant bending or kinking. Such bending or kinking could result in blockage of the catheter 10. The anti-kink elements 44 may be or comprise long thin stiffening elements that are smaller in diameter than the diameter of the catheter, but resist significant bending.

Referring again to FIG. 1, another feature of this embodiment is the provision (optionally) of one or more fluid introduction lumens 50, 52. The fluid lumen 50 optionally allows the introduction of rinse, medication, contrast or other fluids to the distal portion 14 of the catheter 10 within the ileum 16. This can be used to look for leakage, improve discharge of waste, or introduction of therapeutic medication. The fluid lumen 52 optionally allows the introduction of rinse, medication, contrast or other fluids to the third portion 20 of the catheter 10 within the large intestine 22. This can be used to look for leakage, improve hydration by the absorption of water by the large intestine 22, or the introduction of therapeutic medication. Either or both of the lumens 50, 52 may be provided or omitted as desired.

Another feature of this embodiment is the provision (optionally) of one or more radio-opaque features into the catheter 10. The radio-opaque features allow the non-invasive detection of the position of the catheter 10 once it is in place, using for example fluroscopy. Preferably, the radio-opaque features do not obscure the entire extent of the catheter 10, so that other tissue features can continue to be observed. For example, a radio-opaque line 60 may extend generally longitudinally, or helically. Specific shapes 62 may be incorporated to indicate certain features, such as the balloons 30, 40.

Another feature of this embodiment is the provision (optionally) of one or more sensors for providing information to clinicians. For example, a sensor 70 may be provided on or in the catheter 10 at any of the first-fourth portions for detecting an internal parameter of the catheter 10, such as one or more of: a strain sensor to detecting bends or kinks in the waste path; a flow sensor for detecting flow of waste; temperature sensor; pressure sensor for detecting pressure so as to reduce the risk of possible pressure damage to tissue. Such sensors 70 may, or may not, be electronic in nature, generating an electronic output signal. One or more sensors 70 may also be included in the fifth portion 26 of the catheter 10, and/or in the waste collection system coupled to the catheter 10, to monitor parameters such as flow and/or weight of effluent.

Another feature of this embodiment is provision (optionally) of an access port 80 in the catheter 10. The access port 80 may communicate with the drainage lumen 34 of the catheter. The access port 80 may permit the introduction of other catheter-like devices retrospectively into the small intestine (ileum) 16 and/or into the large intestine 22. This can allow the introduction of larger systems such as endoscopes on a temporary basis for clinical assessment or therapy. More than one access port 80 may be provided, and the access ports 80 may communicate with different lumens of the catheter 10.

Another feature of this embodiment is the provision (optionally) of an interface device 90 that terminates the proximal end of the catheter 10, and carries a coupling part 92 for releasably coupling to a collection pouch 94. The releasable coupling may be an adhesive coupling, or a mechanical engagement coupling, or a magnetic coupling. The coupling part 92 may include a coupling flange. The coupling part 92 is fastened to the interface device 90 flexibly, or via a flexible or floating connection so that the ostomy coupling may be separated without removing the interface device 90 and disturbing the catheter 10. The collection pouch 94 may be a conventional ostomy pouch, or a pouch especially designed or configured for the present embodiment.

In an alternative form, the interface device 90 may be replaced by a clamp (not shown) that prevents the catheter 10 from moving inwardly or outwardly with respect to the abdominal wall 24. Optionally, the clamp can be secured to the skin through adhesive or stitches. Alternatively, the clamp might not require securing to the skin if the catheter balloons 30, 40 effectively anchor the catheter 10 and allow tension on the catheter 10 safely. The outlet of the catheter 10 can be directed to a collection pouch 94 as described above.

Figure 6:
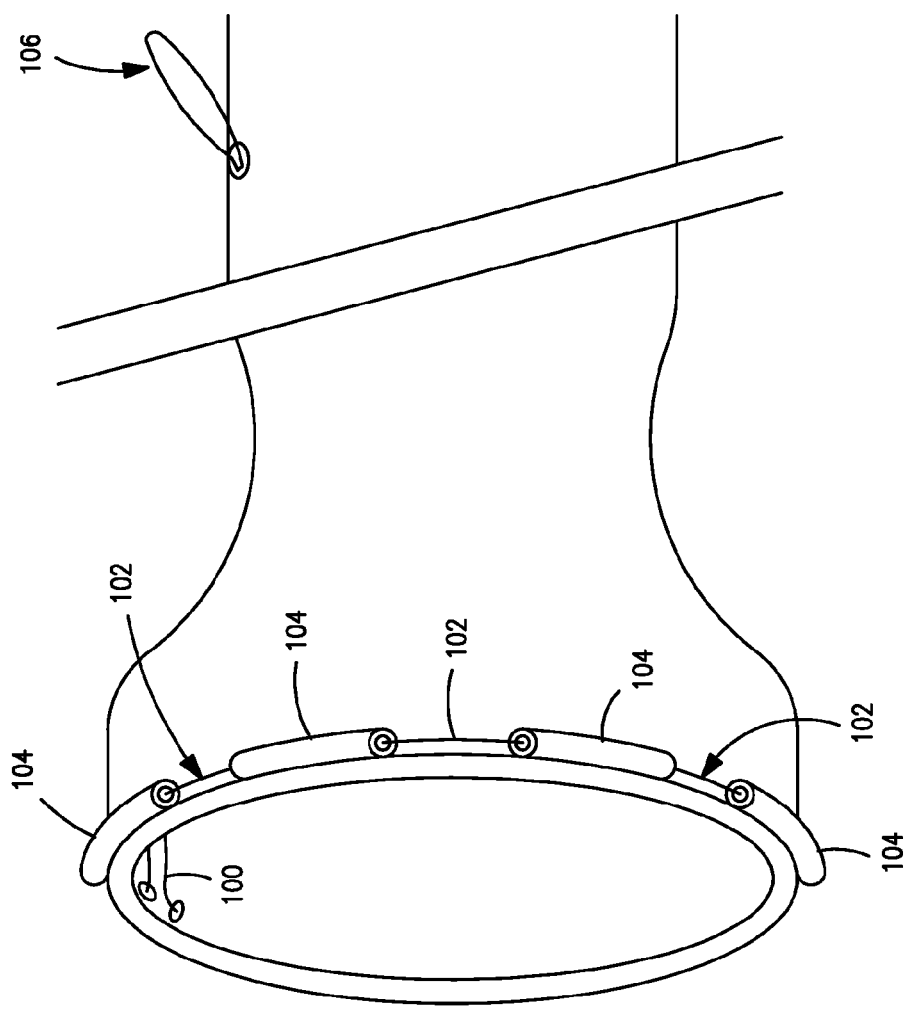
FIG. 6 is a schematic sectional view showing a second embodiment of a temporary ostomy appliance in the form of a transcecal ileostomy appliance, with selectively releasable fastening to surgical sutures or staples.

Referring to FIG. 6, the second embodiment illustrates an alternative sealing and/or fastening technique for establishing a connection between the catheter 10 and internal body tissue, the connection being releasable without surgery. This technique may be used in addition to, or as an alternative to, one or both of the balloons 30, 40. In the second embodiment, a filament 100 provides one or more exposed bridge features 102 that can be secured to internal body tissue, during surgery, by sutures and/or surgical staples. Each bridge feature 102 extends between respective eyes 104. The eyes 104 may be simple apertures, or castellated lugs that space the filament 100 proud from the surface of the catheter 10. The filament 100 extends internally in the catheter 10 to provide a proximal loop, or proximal end, portion 106 at the proximal catheter portion outside the body.

In use, in order to disengage the fastening, the proximal filament portion 106 is cut, or otherwise unfastened, and a free end of the proximal filament portion 106 is then pulled to withdraw the entire filament 100 out of the eyes 104, and out of engagement with the sutures and/or staples. This releases the engagement and allows the catheter 10 to be withdrawn, without the need for removal surgery. The sutures and/or stapes may be made of material that is resorbed by the body over time. The technique of FIG. 6 may be used to enhance the seal between the wall of the ileum 16 and the first portion 14 of the catheter 10, to reduce the risk of effluent leaking around the catheter 10. This may enable the inflation pressure of the blocking balloon 30 (if implemented) to be reduced, while still achieving a reliable blocking and seal function. Alternatively, it may replace the need for the blocking balloon 30 by achieving a reliable seal by sutures/staples. The ability to disengage the catheter 10 by removing the filament 100 enables the catheter 10 to be disengaged from the ileum wall tissue, without surgery. The same technique may be used to fasten the catheter 10 with respect to the large intestine wall. Multiple filaments 100 may be used if desired at the same fastening site, or at different fastening sites.

Figure 7:
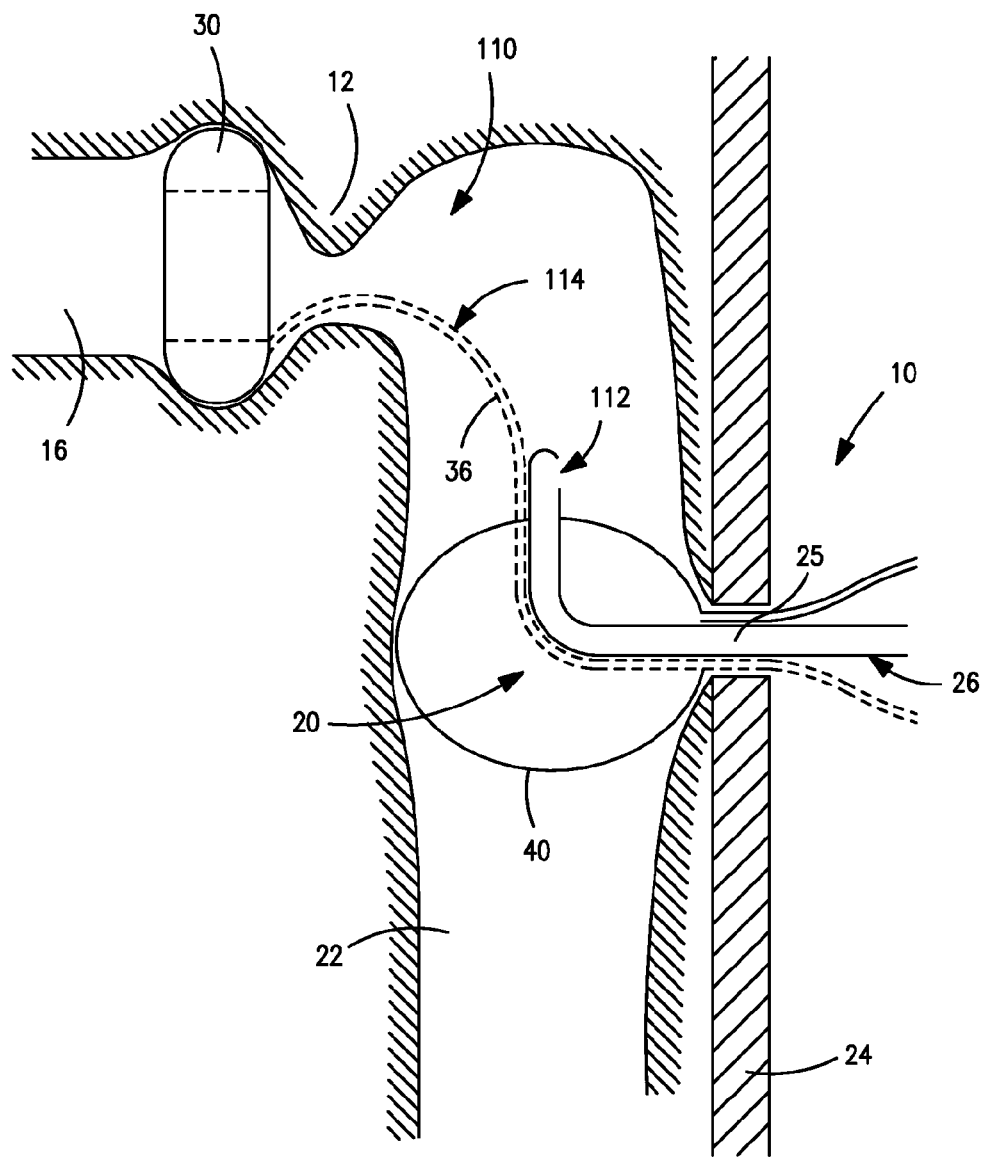
FIG. 7 is a schematic sectional view showing a third embodiment of temporary ostomy appliance.

Referring to FIG. 7, a third embodiment of the temporary ostomy appliance comprises a catheter 10 inserted through the abdominal wall 24 and into at least the large intestine 22. As described below, the catheter 10 may optionally include a transcecal portion 110 that extends through the cecal valve 12. A difference between the first embodiment and the present embodiment is that, whereas in the first embodiment effluent is diverted into the catheter 10 from within the small intestine 16, in the present embodiment, effluent is diverted into the catheter 10 from within the large intestine 22.

In the following description, the order of reference of the portions of the catheter 10 is reversed compared to the description of the first embodiment, but this is merely for ease of description. The catheter 10 comprises a first proximal portion 26 intended to extend outside the body, a second portion 25 intended to pass through the abdominal wall 24, and a third portion 20 intended to be received in the large intestine 22. An inflatable cuff or balloon 40 is provided at the third portion 20. The balloon 40 serves to block, in the large intestine 22, passage of effluent coming from cecal valve 12, and divert the effluent into the catheter 10 at an inlet aperture 112. In this embodiment, the catheter 10 may be disposed anywhere along the length of the large intestine 22, and preferably at least about 10 cm away from the cecal valve 12.

As mentioned above, the catheter 10 may optionally include a transcecal portion 110. The transcecal portion 110 may serve as an anchor for the catheter 10, to ensure that the inlet aperture 112 of the third portion 20 is always disposed facing towards the cecal valve 12. In other words, transcecal portion 110 ensures that the inlet aperture 112 is on the upstream side of the balloon 40 (with respect to effluent flow in the large intestine 22). The transcecal portion 110 may prevent, or at least obstruct, any accidental rotation of the catheter 10 about the aperture in the abdominal wall 24, which might otherwise turn the inlet aperture 112 towards the intestinal side wall or even towards the downstream side, and thereby cause undesired blockage of drainage. If the effluent is not free to drain into the catheter 10, this creates a total blockage in the intestine, increasing the pressure of effluent pressing on the balloon 40, and increasing the risk of leakage of effluent past the balloon 40.

The optional transcecal portion 110 may optionally comprise an inflatable cuff or balloon 30 intended to be received in the ileum 16 of the small intestine, and one or more flexible links 114 joining the balloon 30 to the third portion 20 of the catheter 10. The balloon 30 is not intended to block passage of effluent, and may have any shape suitable for locating behind the cecal valve 12 while not creating a blockage to effluent. For example, a suitable shape is a toroid or doughnut shape with an open center. The flexible link(s) 114 includes an inflation lumen 36, similar to the inflation lumen 36 of the first embodiment. The flexible link(s) 114 may be catheter-like, or it may be filament like. The flexible link(s) does not have to contain effluent, but merely joins the balloon 30 to the third portion 20 of the catheter 10, in order to anchor the orientation of the third portion 20 with respect to the cecal valve 12.

The blocking and fixation functions of the balloons 30, 40 are reversed compared to the balloons of the first embodiment. In the present embodiment, the more distal balloon 30 does not have to perform any blocking function, allowing a lower inflation pressure. The constructions of the balloons 30, 40 may be similar to the balloons 30, 40 of the first embodiment. Either balloon 30, 40 may be made of elastically stretchable material. However, it is preferred that one or both of the balloons 30, 40 be pre-shaped so that the balloon material does not stretch when the balloon 30, 40 is inflated in use, allowing lower inflation pressures.

The balloon 40 may be supplemented by the removable bridge features 102 of the second embodiment, and this removable fastening may render the transcecal portion 110 of the catheter 10 unnecessary if the balloon 40 is sufficiently anchored, by the removable bridge features 102 or other means, against unwanted turning in the large intestine 22. If the transcecal portion 110 is implemented, the transcecal portion 110 may also include one or more removable bridge features 102. Such a releasable fastening may supplement the balloon 30, or the balloon 30 may be omitted from the transcecal portion 110.

The temporary ostomy appliance of the third embodiment may be removed without surgery in a similar manner to the first (and/or second) embodiment. The fixation balloon 40 is deflated, and the blocking balloon 30 (if implemented) is also deflated. This allows easy withdrawal of the catheter 10 without additional surgery.

Figure 8:
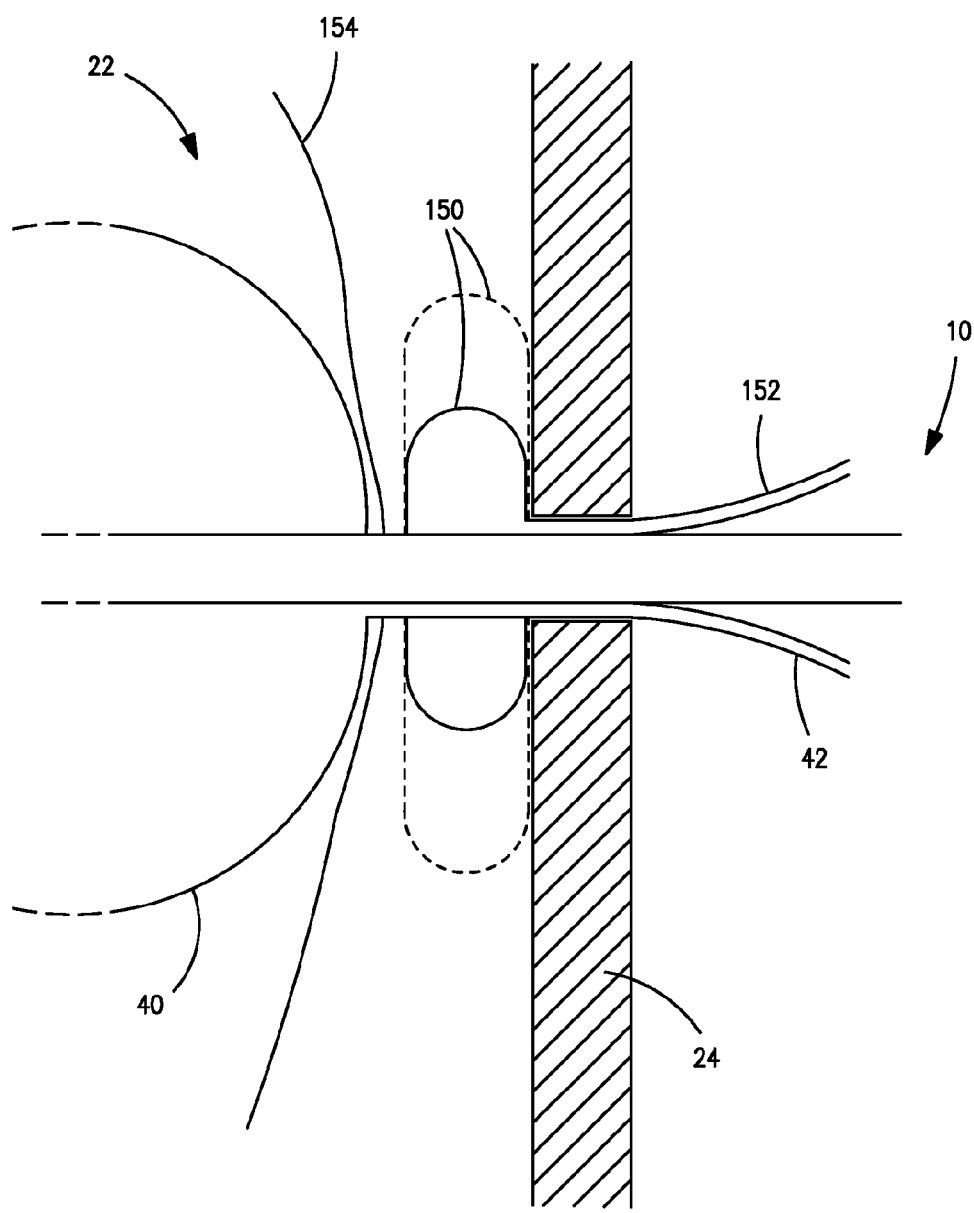
FIG. 8 is a schematic sectional view showing a fourth embodiment of temporary ostomy appliance.

Referring to FIG. 8, a fourth embodiment of temporary ostomy appliance is illustrated. The fourth embodiment may be used independently, or it may be combined with any of the features of any of the preceding embodiments. Whereas in the first-third embodiments, the appliance generally draws the large intestine 22 directly up against the abdominal wall 24 at the site where the catheter 10 passes through the abdominal wall 24 and/or enters the large intestine 22, in the present embodiment, a fender 150 is provided to separate and/or cushion the outside surface of the wall 154 of the large intestine 22 from direct contact with the abdominal wall 24. The fender 150 may serve to prevent tissue damage to the wall of the large intestine 22 that might otherwise result from abrasion and compression against the abdominal wall 24, and may also reduce the risk of fistulae. The fender 150 may encircle the catheter 10. For example, the fender 150 may be doughnut or toroidal in shape. The fender 150 may be relatively small (as illustrated) or it may be relatively large (as indicated in broken line). The fender 150 outside the large intestine 22 and a balloon 40 inside the large intestine 22 may sandwich and/or cushion the intestinal wall 154 from both sides at the site where the catheter 10 enters the large intestine 22.

The fender 150 may be expandable and/or collapsible to facilitate insertion and removal. The fender 150 may comprise an inflatable balloon or cuff, similar to the balloons 30, 40 described previously. The fender 150 balloon is inflatable/deflateable by means of an inflation lumen 152, similar to the inflation lumens 36, 42 described previously. Prior to insertion of the catheter 10, the fender 150 balloon is deflated to a compact shape, allowing insertion through a relatively small aperture in the abdominal wall 24. Thereafter, the fender 150 balloon is inflated (e.g., in sequence with the balloon 30, 40), to act as the fender 150 separating the wall of the large intestine 22 from the abdominal wall 24 when the appliance is secured. Later, when it is desired to remove the appliance, the fender balloon is deflated by evacuating the inflation fluid via the inflation lumen 152 (in a similar manner to the other balloon(s) 30, 40), allowing removal of the appliance without a surgical closure procedure. The fender balloon may be similar to the balloons 30, 40 of the first embodiment. The fender balloon may be made of elastically stretchable material, or the fender balloon may be pre-shaped so that the balloon material does not stretch when the balloon is inflated in use, allowing a lower inflation pressure.

If desired, the fender 150 may be releasably secured in position by one or more suturable bridges 102 of the embodiment of FIG. 6.

The device may be assembled from separate components to achieve the appropriate configuration at the time of placement.

Many modifications and equivalents to the invention are possible without departing from the scope and/or principles of the invention as claimed.

I claim:

1. A temporary ostomy appliance comprising:
a catheter for extending through the abdominal wall into the large intestine, the catheter including an inlet aperture for drainage of effluent from the large intestine;
an inflatable balloon disposed on the catheter for blocking the passage of effluent in the large intestine, and diverting effluent through the inlet aperture for drainage via the catheter; and
a fender disposed on the catheter and separate from the inflatable balloon for separating the outside surface of the intestinal wall from direct contact with the inner abdominal wall at the site where the catheter enters the intestine.

2. The temporary ostomy appliance of claim 1 wherein the catheter is transcecal extending
through the abdominal wall into the large intestine and through the cecal valve into the ileum, the catheter including a first tubular portion intended to be received in the ileum, and a second tubular portion intended to be received at the cecal valve, the first and second tubular portions defining a drainage channel therein, and the second tubular portion being more easily collapsible, to collapse the drainage channel, than the first tubular portion.

3. The temporary ostomy appliance of claim 2, wherein the second tubular portion has a thinner wall thickness than the first tubular portion.

4. The temporary ostomy appliance of claim 2, wherein the second tubular portion is made of a more compliant material with a lower Youngs Modulus or durometer than the first tubular portion.

5. The temporary ostomy appliance of claim 2, wherein the second tubular portion is collapsible to less than about 1 cm in external diameter when the catheter is empty, without compression of the catheter wall material.

6. The temporary ostomy appliance of claim 2, wherein the second tubular portion is expandable to greater than about 1 cm in external diameter when passing effluent, without stretching of the catheter wall material.

7. The temporary ostomy appliance of claim 2, wherein the first and second tubular portions are made of material selected from: silicone; and/or polyurethane, and/or another polymer material.

8. The temporary ostomy appliance of claim 2, further comprising a third tubular portion intended to be received in the large intestine, the second tubular portion being more easily collapsible, to collapse the drainage channel, than the third tubular portion.

9. The temporary ostomy appliance of claim 1 wherein the inflatable balloon is made of flexible material defining a hollow bladder of predetermined size that is not substantially smaller than the size of the balloon when inflated in use against the intestinal tissue.

10. The temporary ostomy appliance of claim 9, wherein the balloon is inflatable to said predetermined size without elastic stretching of the balloon wall material.

11. The temporary ostomy appliance of claim 9, wherein said predetermined size is significantly greater than the size of the balloon when inflated in use in the intestine.

12. The temporary ostomy appliance of claim 9, wherein the balloon comprises material of a thickness of about 100 microns or less.

13. The temporary ostomy appliance of claim 1 wherein the catheter includes a first portion accessible in use from outside the abdominal wall and a second portion that is received in use inside the body; and
a filament that extends between first and second eyes at the second catheter portion, to define a bridge feature that is fastenable to internal body tissue during surgery by a surgical suture or a surgical staple, the filament extending to the first portion of the catheter;
wherein in use, the filament is withdrawable from the eyes by pulling on a portion of the filament at the first portion.

14. The temporary ostomy appliance of claim 13, wherein the eyes comprise lugs that space the filament proud of the surface of the catheter.

15. The temporary ostomy appliance of claim 14, wherein the filament extends from the eyes to the first portion, via an internal passage in the catheter.

16. The temporary ostomy appliance of claim 15, wherein the filament passes to the exterior of the catheter near or at the first portion.

17. The temporary ostomy appliance of claim 1 wherein the catheter is transcecal extending through the abdominal wall into the large intestine, and through the cecal valve into the ileum, the catheter comprising:
a first lumen for drainage of material from the ileum through the catheter; and
a second lumen for communicating with an interior of the large intestine and/or the ileum, for permitting admission of fluid or separate instrumentation thereto.

18. The temporary ostomy appliance of claim 1 wherein the catheter is transcecal extending through the abdominal wall into the large intestine, and through the cecal valve into the ileum, and includes at least one sensor for measuring a parameter of the catheter or catheter contents in use.

19. The temporary ostomy appliance of claim 18, wherein the sensor is configured to generate an electronic output signal.

20. The temporary ostomy appliance of claim 18, wherein the sensor is selected from a group consisting of a strain sensor; a temperature sensor; a flow sensor; a weight sensor; a pressure sensor.

21. The temporary ostomy appliance of claim 18 wherein: the catheter further comprises at least one longitudinally extending stiffening element for resisting kinking of the catheter.

22. The temporary ostomy appliance of claim 1 wherein the catheter is transcecal for extending from a proximal portion through the abdominal wall into the large intestine, through the cecal valve and into the ileum, the catheter include a lumen for communicating with an interior space of the large intestine and/or ileum, and the catheter further comprising a closable access port at the proximal portion for permitting insertion of additional catheters into the lumen.

23. The temporary ostomy appliance of claim 1, further comprising a transcecal extension that extends from the large intestine, through the cecal valve into the ileum.

24. The temporary ostomy appliance of claim 23, wherein the transcecal extension further comprises an inflatable balloon at a distal portion for locating the distal portion in the ileum.

25. The temporary ostomy appliance of claim 23, wherein the inlet aperture is configured to be at least 10 cm from the cecal valve, in use.

26. The temporary ostomy appliance of claim 1, wherein the fender is selectively expandable and/or collapsible.

27. The temporary ostomy appliance of claim 1, wherein the fender comprises an inflatable fender balloon.

28. The temporary ostomy appliance of claim 1, wherein the inflatable balloon and the fender are configured to sandwich the intestinal wall between the inflatable balloon and the fender at the site where the catheter enters the intestine.

29. The temporary ostomy appliance of claim 1, wherein the catheter is a transcecal catheter for extending into the large intestine, and through the cecal valve into the ileum.

* * * * *